United States Patent
Saito et al.

(10) Patent No.: US 10,436,783 B2
(45) Date of Patent: Oct. 8, 2019

(54) METHOD FOR MICROBIAL ANTIGEN COLLECTION

(71) Applicant: DENKA SEIKEN CO., LTD, Chuo-ku, Tokyo (JP)

(72) Inventors: Yuji Saito, Niigata (JP); Daisuke Kato, Niigata (JP)

(73) Assignee: Denka Seiken Co., Ltd., Tokyo (JP)

( * ) Notice: Subject to any disclaimer, the term of this patent is extended or adjusted under 35 U.S.C. 154(b) by 20 days.

(21) Appl. No.: 15/569,143

(22) PCT Filed: Apr. 28, 2016

(86) PCT No.: PCT/JP2016/063310
§ 371 (c)(1),
(2) Date: Oct. 25, 2017

(87) PCT Pub. No.: WO2016/175269
PCT Pub. Date: Nov. 3, 2016

(65) Prior Publication Data
US 2018/0143195 A1   May 24, 2018

(30) Foreign Application Priority Data

Apr. 28, 2015 (JP) ................................. 2015-092218

(51) Int. Cl.
| | |
|---|---|
| G01N 33/53 | (2006.01) |
| G01N 33/569 | (2006.01) |
| C12N 1/00 | (2006.01) |
| C12Q 1/04 | (2006.01) |
| C12N 1/06 | (2006.01) |
| G01N 33/543 | (2006.01) |
| C07K 1/36 | (2006.01) |
| C07K 14/195 | (2006.01) |

(52) U.S. Cl.
CPC ......... *G01N 33/56938* (2013.01); *C07K 1/36* (2013.01); *C07K 14/195* (2013.01); *C12N 1/00* (2013.01); *C12N 1/06* (2013.01); *C12Q 1/04* (2013.01); *G01N 33/543* (2013.01); *G01N 33/569* (2013.01)

(58) Field of Classification Search
None
See application file for complete search history.

(56) References Cited

U.S. PATENT DOCUMENTS

| | | |
|---|---|---|
| 2012/0064538 A1 | 3/2012 | Ito |
| 2013/0309700 A1 | 11/2013 | Hearn et al. |

FOREIGN PATENT DOCUMENTS

| | | |
|---|---|---|
| EP | 03630110 A2 | 4/1990 |
| JP | 08-502413 A | 3/1996 |
| JP | 2003-189895 A | 7/2003 |
| JP | 2004-279113 A | 10/2004 |
| WO | WO 94/10336 A1 | 5/1994 |
| WO | WO 2007/069673 A1 | 6/2007 |

OTHER PUBLICATIONS

International Search Report dated Jul. 26, 2016, in PCT/JP2016/063310.
Supplementary European Search Report dated Oct. 10, 2018, in EP 16786545.0.
Office Action dated Jul. 23, 2019, in JP 2015-092218.

*Primary Examiner* — Gary Counts
(74) *Attorney, Agent, or Firm* — Foley & Lardner LLP

(57) ABSTRACT

This invention provides a method for easily collecting antigens possessed by microorganisms without the use of special equipment. The method for collecting microbial antigens comprises: allowing a specimen containing microorganisms to pass through a filter membrane with a pore diameter that does not allow microorganisms to pass therethrough; capturing the microorganisms in the specimen on the filter membrane; applying a microbial destruction reagent capable of microbial membrane destruction to the filter membrane comprising the microorganisms captured thereon to destruct the captured microorganisms on the filter membrane; and collecting antigens in the filtrate.

15 Claims, 1 Drawing Sheet

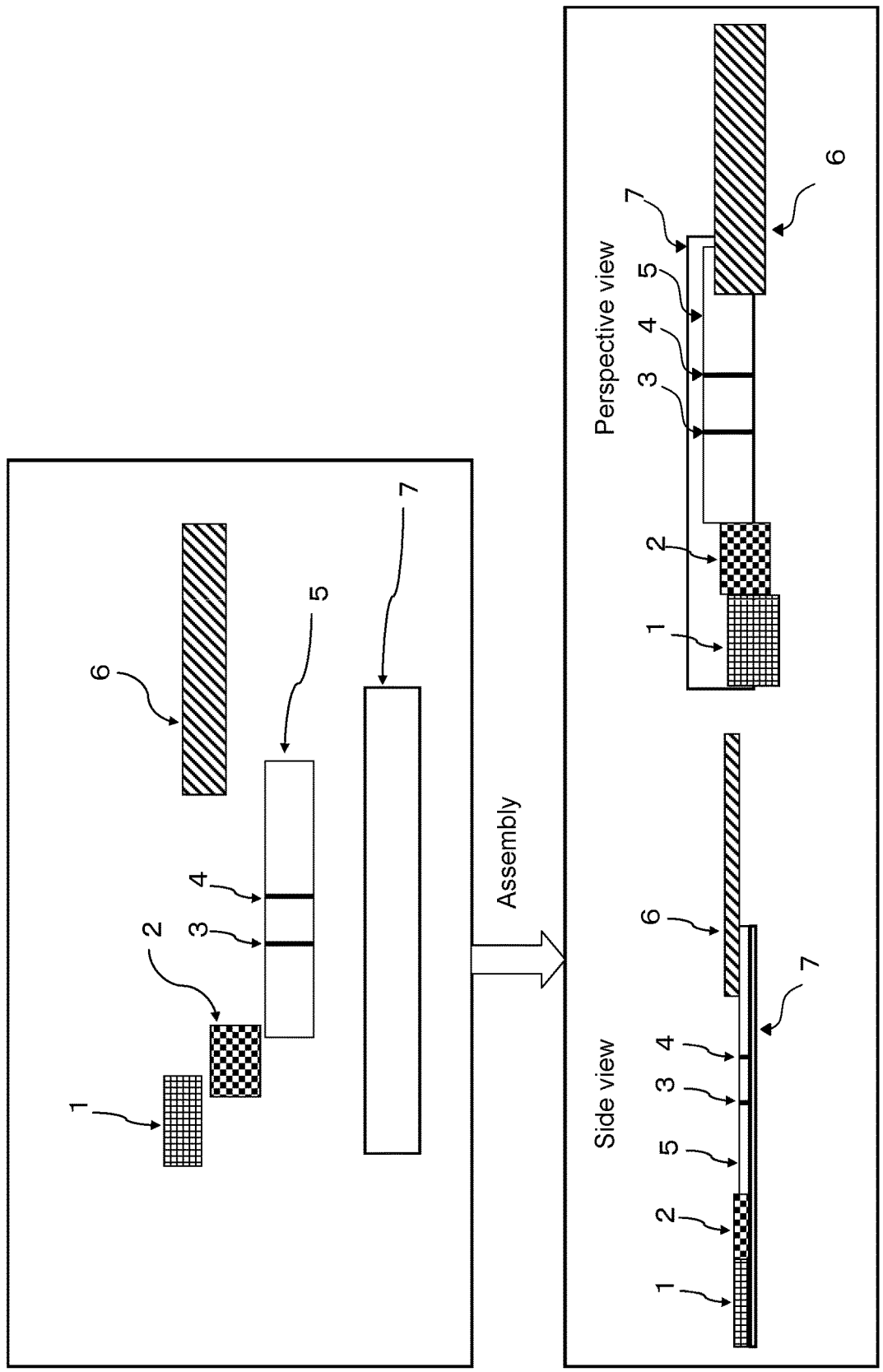

METHOD FOR MICROBIAL ANTIGEN COLLECTION

CROSS-REFERENCE TO RELATED APPLICATIONS

This application is a National Stage application of PCT/JP2016/063310, filed Apr. 28, 2016, which claims priority from Japanese application JP 2015-092218, filed Apr. 28, 2015.

TECHNICAL FIELD

The present invention relates to a method for collecting microbial antigens.

BACKGROUND ART

In the case of infectious diseases such as septicemia, administration of adequate antibacterial agents at an early stage is critical for treatment or prognosis of a patient. According to conventional techniques, infectious diseases such as septicemia have been tested in the manner described below.

The blood sampled from a patient (2 to 10 ml) is inoculated into about 30 to 100 ml of a liquid medium for bacterial culture, and culture is then conducted at 30° C. to 37° C. On the basis of changes in the turbidity of the medium, generation of gas in the medium caused by bacteria, changes in pH levels, and other factors as indicators, observation is continued for 1 to 7 days until bacterial growth is detected. After the bacterial growth is observed, the culture solution is collected and subjected to gram staining and subculture (secondary culture). Bacterial species are roughly classified on the basis of the results of gram staining, and whether a single type of bacteria or plural types of bacteria are detected is determined. When colonies of the bacteria grown via subculture are homogeneous, it is hypothesized that a single type of bacteria is present in the blood, and the bacteria are then subjected to the identification test and the sensitivity test. When a plurality of types of bacteria are observed as a result of gram staining or colonies of apparently different configurations are grown, in contrast, each colony is picked, and culture is continued until colonies of a single configuration are selectively grown. That is, it takes a number of days to complete a procedure from sampling of specimens to identification thereof. In the case of a patient suspected of septicemia, early diagnosis and administration of an adequate antibacterial agent are critical for prognosis of the patient. As a method that enables more accurate identification of bacterial species within a shorter period of time, accordingly, an immunological technique, such as immunochromatography, is employed (WO 2007/069673). When bacteria are identified via an immunological technique, an immunoglobulin that specifically recognizes a protein of the target bacteria is to be bound. The bound immunoglobulin is labeled with colored latex particles or fluorescence materials in advance, so that the presence of bacteria can be detected. Thus, bacteria can be detected directly from blood culture without pure culture. However, specimens used for bacterial testing, such as the blood, culture solution, sputum, snivel, or stool, contain various types of proteins. In order to detect a target protein with high sensitivity, accordingly, it is necessary to remove contaminants by separating bacteria via centrifugation or culture on a solid medium. In addition, thermal treatment, cell membrane destruction with the aid of a solution, or other treatment may become necessary depending on the place where a protein of target bacteria is present, a protein configuration, or other factors.

Accordingly, special equipment, such as a centrifuge or heat block, was necessary, and a time-consuming procedure, such as culture, was necessary. In the case of centrifugation, furthermore, precipitated bacteria may erroneously be suctioned when discarding the supernatant, the number of bacteria may be reduced, and accurate judgment may not be made occasionally.

SUMMARY OF THE INVENTION

Objects to be Attained by the Invention

The present invention provides a method for easily collecting antigens possessed by microorganisms without the use of special equipment.

Means for Attaining the Objects

The present inventors have conducted concentrated studies concerning a method for easily detecting microorganisms, such as pathogenic bacteria. Microorganisms can be detected by measuring antigens possessed by microorganisms of interest. Accordingly, the present inventors examined a method for easily collecting antigens.

As a result, they discovered that microorganisms could be rapidly destructed and antigens could then be easily collected by allowing microorganisms contained in specimens such as the blood or culture solution to pass through a filter membrane to capture the microorganisms on the membrane and treating the bacteria captured on the membrane with a solution containing a surfactant or the like. This has led to the completion of the present invention.

Specifically, the present invention is as described below.
[1] A method for collecting antigens of microorganisms comprising: allowing specimens containing microorganisms to pass through a filter membrane with a pore diameter that does not allow the microorganisms to pass therethrough; capturing the microorganisms in the specimens on the filter membrane; allowing a microbial destruction reagent capable of microbial membrane destruction to pass through the filter membrane on which the microorganisms are captured to destruct the captured microorganisms on the filter membrane; and collecting the antigens in the filtrate.
[2] The method for collecting antigens of microorganisms according to [1], wherein the microorganisms are bacteria.
[3] The method for collecting antigens of microorganisms according to [1], wherein the microbial destruction reagent is a surfactant, an alkaline solution, or a mixture of a surfactant and an alkaline solution.
[4] The method for collecting antigens of microorganisms according to [3], wherein the alkaline solution has a pH of 11 or higher.
[5] The method for collecting antigens of microorganisms according to [3], wherein the alkaline solution is a sodium hydroxide solution.
[6] A method for detecting microorganisms comprising assaying the microbial antigens collected by the method according to any of [1] to [5] by an immunoassay technique.
[7] The method for detecting microorganisms according to [6], wherein the immunoassay technique is immunochromatography.

This description contains part or all of the disclosure of Japanese Patent Application No. 2015-092218, based on which the present application claims a priority.

Effects of the Invention

According to the method of the present invention, specimens, such as the blood or culture solution, containing microorganisms such as bacteria are allowed to pass through a filter membrane, the microorganisms are captured on the filter membrane, and the microorganisms contained in the specimens can be easily separated from contaminants. In addition, a microbial destruction reagent containing a surfactant or/and an alkaline solution is allowed to pass through a filter membrane, so that the microorganisms captured on the membrane are destructed, and the antigens possessed by the microorganisms are exposed and easily collected. According to the method of the present invention, antigens of microorganisms can be easily collected without the use of special equipment. By assaying the collected antigens, the presence or absence of microorganisms can be detected, and, for example, microbial infections can be diagnosed.

BRIEF DESCRIPTION OF THE DRAWING

FIG. 1 shows an embodiment of a detection apparatus that can be used for assaying the antigens collected by the method of the present invention.

EMBODIMENTS FOR CARRYING OUT THE INVENTION

Hereafter, the present invention is described in detail.

1. Collection of Microbial Antigens

Microorganisms from which antigens can be collected by the method of the present invention are not particularly limited. Examples of such microorganisms include bacteria, algae, protists, fungi such as yeast and mold, and eukaryotes such as slime molds. Among such microorganisms, pathogenic microorganisms causing infectious diseases in humans or non-human animals are preferable. Examples thereof include *Staphylococcus aureus* including methicillin resistant *staphylococcus aureus* (MRSA); *Escherichia coli* including enteropathogenic *Escherichia coli*; bacteria, such as *Salmonella, Pseudomonas*, cholera *vibrio, Bacillus dysenteriae*, anthrax *bacillus, Bacillus tuberculosis, Clostridium botulinum, Clostridium tetani*, chain coccus, *Campylobacter*, Welch *bacillus, Vibrio parahaemolyticus, Chlamydia trachomatis, Streptococcus haemolyticus, Bordetella pertussis, Helicobacter pylori, Leptospira, Treponema pallidum*, and *Borrelia; Candida albicans; Trichophyton*; and *Aspergillus*.

Specimens to be analyzed as to the presence of microorganisms therein by the method of the present invention are not limited. Examples thereof include biological samples, such as a throat swab, a nasal swab, a nasal aspirate, a stool suspension, blood plasma, blood serum, urine, saliva, amnion liquid, spinal fluid, pus, organ extract, and various tissue extracts; a food extract; a culture supernatant; tap water; waste water; lake water; river water; seawater; a soil extract; and a sludge extract. From the viewpoint of detection of pathogenic microorganisms, biological samples are particularly preferable. For example, a throat swab, a nasal swab, a nasal aspirate, a nasal wash, an alveolar wash, a rectal swab, or a stool suspension can be preferably used. Human-derived or non-human animal-derived specimens can be used. Also, a culture solution in which the above mentioned specimens was cultured is within the scope of the specimens. While a specimen may be used without any processing, a specimen that contains an excess amount of microorganisms, such as a culture solution, a highly viscous specimen, or the like is adequately used in the form of a suspension thereof in, for example, physiological saline or a buffer. A liquid in which the specimen is to be suspended is referred to as a "liquid for specimen suspension," and a liquid comprising the specimen suspended in the liquid for specimen suspension is referred to as a "specimen suspension." When a specimen contains blood such as whole blood, it is preferable that blood erythrocytes be destructed with the use of a surfactant or the like in advance and completely hemolyzed. In order to attain hemolytic reaction, a specimen may be treated with the use of, for example, a surfactant, various solvents, or a hypotonic solution.

According to the method of the present invention, the specimen is allowed to pass through a filter membrane, so as to capture microorganisms on the filter membrane. When microorganisms are captured, microorganisms are not allowed to pass through a filter membrane, and they remain on the filter membrane after the specimen has passed therethrough. In this case, a filter membrane having a pore diameter that does not allow microorganisms to pass therethrough is used.

When microorganisms to be detected are bacteria, a filter membrane with a pore diameter that is 1.5 µm or less, preferably 1.2 µm or less, more preferably 0.8 µm or less, and further preferably 0.45 µm or less, for example, a filter membrane with a pore diameter that is 0.1 to 1.2 µm, and preferably 0.22 µm, 0.45 µm, 0.8 µm, or 1.2 µm, may be used. When large-size mold or yeast is to be detected, a filter membrane with a pore diameter that is larger than 0.5 µm, such as a filter membrane with a pore diameter that is 0.8 µm, may be used. Examples of filter membranes that can be used include filter membranes with the pore diameters as described above and composed of mixed cellulose esters (MCE), polyvinylidene fluoride (PVDF), polytetrafluoroethylene (PTFE), hydrophilic PTFE, polyethersulfone (PES), hydrophilic polyethersulfone, hydrophilic polypropylene (GHP), nylon (NYL), cellulose acetate (CA), polysulfone (PSF), an acrylic copolymer, polyamide, Nylon 66, polyester, polycarbonate, nitrocellulose, and a mixture of nitrocellulose and cellulose ester. In combination with such a filter membrane, a prefilter made of glass fiber, such as borosilicate glass fiber (GF) or multi-layered glass fiber (GxF), may be used. Examples of such combinations include a nylon filter membrane and a multi-layer glass fiber (GxF) prefilter, a polyethersulfone (PES) filter membrane and a multi-layer glass fiber (GxF) prefilter, a cellulose acetate (CA) filter membrane and a borosilicate glass fiber (GF) prefilter, and a nylon (NYL) filter membrane and a borosilicate glass fiber (GF) prefilter.

After microorganisms are captured on a filter membrane, the captured microorganisms are destructed to expose microbial antigens. Microorganisms are preferably destructed by means of microbial cell membrane destruction. Antigens exposed as a result of destruction of microorganisms can be easily collected. Examples of microbial antigens include substances that can produce antibodies, such as proteins, lipids, and polysaccharides. This indicates that collectedantigens are detected with the use of antigen-antibody reactions. Specific examples of such substances include constituents of the microorganisms, toxins produced by the microorganisms, and bacterial antigens of the bacteria. A more specific example is penicillin-binding protein 2' (PBP2') of MRSA.

The captured microorganisms are destructed by treating the microorganisms with a microbial destruction reagent containing a surfactant or/and a microbial destruction reagent, which is an alkaline solution. A microbial destruction reagent is capable of destructing a microbial membrane. A surfactant to be used is not limited, and a surfactant that is capable of solubilizing a microbial membrane is preferably used. Examples of surfactants that can be used include: polyoxyethylene p-t-octylphenyl ether (TRITON-based surfactants), such as TRITON X-100 (TRITON: registered trademark) (polyoxyethylene (10) octylphenyl ether), TRITON X-114 (polyoxyethylene (8) octylphenyl ether), TRITON X-405 (polyoxyethylene (40) isooctylphenyl ether), and NP-40 (Nonidet P-40) (polyoxyethylene (9) octylphenyl ether); polyoxyethylene sorbitan fatty acid ester (TWEEN-based surfactants), such as TWEEN 20 (TWEEN: registered trademark), TWEEN 40, TWEEN 60, TWEEN 80, TWEEN 65, and TWEEN 85; polyoxyethylene alkylether (Briji-based surfactants), such as Briji 35 (Briji: registered trademark) (polyoxyethylene (23) lauryl ether); nonionic surfactants, such as dodecyl-β-D-maltose and octyl-β-D-glucoside; anionic surfactants, such as sodium dodecyl sulfate (SDS); cationic surfactants, such as benzalkonium chloride, benzethonium chloride, didecyldimethylammonium salt, and dodecyltrimethylammonium chloride; and amphoteric surfactants, such as CHAPS (3-(3-cholamidepropyl)dimethylammonio-1-propane sulphonate) and alkyl polyaminoethyl glycine chloride. Use of nonionic surfactants, such as ether-based surfactants (e.g., polyoxyethylene alkylether, polyoxyethylene alkyl allyl ether, and polyoxyethylene polyoxypropylene glycol) and ester-based surfactants (e.g., higher alcohol fatty acid ester), and ester ether-based surfactants (e.g., polyoxyethylene sorbitan fatty acid ester), anionic surfactants, and amphoteric surfactants is preferable, and use of nonionic surfactants is particularly preferable. A surfactant may be used at a concentration of 0.2 to 5% (w/w), and preferably 0.5 to 2% (w/w).

An alkaline solution not only destructs microbial membranes but also denature protein A in the membrane. Thus, nonspecific reactions to antibodies can be suppressed. An alkaline solution with a pH level of 11 or higher, preferably 12 or higher, and more preferably 13 or higher may be used. For example, a 0.1 M to 1.0 M sodium hydroxide solution or sodium hypochlorite is preferably used.

A surfactant may be mixed with an alkaline solution and used in the form of a mixture. For example, 0.1 to 0.5 M sodium hydroxide containing a surfactant, such as 1% to 2% TRITON X-100, can be used.

Microorganisms may be treated with a microbial destruction reagent by applying a surfactant or an alkaline solution to the filter membrane on which microorganisms have been captured. Specifically, the microbial destruction reagent may be brought into contact with the captured microorganisms. Thereafter, the filter membrane may be allowed to stand for 1 to 20 minutes, and preferably 2 to 10 minutes, while the solution is retained therein. Thus, microorganisms can be completely destructed. When a filter membrane with a diameter of 20 to 40 mm is used, for example, 1 to several ml of the specimen or specimen suspension is applied to the filter membrane, and microorganisms in the specimen or specimen suspension are then captured on the filter membrane. Subsequently, several to several hundred ml of the microbial destruction reagent is applied to the filter membrane, so as to destruct the microorganisms captured on the filter membrane and collect a filtrate containing microbial antigens. When the microbial destruction reagent is an alkaline solution, several to several hundred ml of a buffer with a pH around neutral, preferably 1/10 to 2/3 volume of the microbial destruction reagent used is added so as to neutralize the reagent or reduce the surfactant concentration. A solution to be added to the collected filtrate is referred to as a filtrate-adjusting solution, and an adequate reagent may be selected depending on the conditions for a method for assaying antigens in the collected filtrate. As a filtrate-adjusting solution, a neutral to acidic buffer, such as a Tris-HCl buffer, may be used. The collected filtrate contains microbial antigens. Antigens contained in the collected filtrate can be assayed by various techniques. A filtrate-adjusting solution may be applied to the filter membrane through which the microbial destruction reagent has passed. Thus, microbial antigens can be collected while neutralizing the microbial destruction reagent or lowering the surfactant concentration.

The liquid for specimen suspension, a microbial destruction reagent, and a filtrate-adjusting solution, in total, is referred to as microbial antigen extraction reagents.

2. Assay of Collected Antigens

Collected antigens can be assayed by any technique. Preferably, an immunoassay technique based on the antigen-antibody reactions is performed with the use of an antibody specific to the target antigen. Examples of immunoassay techniques include immunostaining such as fluorescence antibody technique, enzyme antibody technique, heavy metal-labeled antibody technique, and radioisotope-labeled antibody technique; a method involving separation via electrophoresis in combination with detection with the aid of a fluorescence, enzyme, or radioisotope such as Western blotting and fluorescence two-dimensional electrophoresis, enzyme-linked immunosorbent assay (ELISA), dot-blotting, latex agglutination-turbidimetric immunoassay (LA:TI), and immunochromatography. The immunochromatography or ELISA is preferable.

Immunochromatography is carried out with the use of an immunochromatographic detection apparatus. An immunochromatographic detection apparatus is also referred to as an immunochromatographic test piece. The detection apparatus is an immunochromatographic test piece composed of test pieces. For example, the test pieces are arranged as shown in FIG. 1. The detection apparatus comprises: a specimen supply site 1 that supplies a specimen onto a sheet-like solid-phase support; a labeled reagent site 2 that retains a labeled reagent that has labeled an antibody binding specifically to an antigen on a solid-phase support in a spreadable manner thereon; and a capture reagent site 3 on which a capture reagent capable of specifically binding to and capturing an antigen-labeled reagent complex has been immobilized. It is composed such that the specimen successively passes through the labeled reagent site 2 and the capture reagent site 3 in that order, once a specimen is supplied to the specimen supply site 1.

The immunochromatographic detection apparatus according to the present invention may further comprise a control reagent in a control site, and, in addition, it may comprise an absorption site. A control reagent is not limited. For example, a substance to which an antibody in the labeled reagent binds can be used. A control reagent may be fixed at a site downstream of the capture reagent site, which corresponds to "Control site 4" in FIG. 1. An absorption site has a liquid absorbing property, so that it absorbs a specimen that has passed through the capture reagent site, so as to regulate the flow of the specimens. The absorption site may be located in the lowermost position of the detection apparatus, which corresponds to "Absorption site 6" in FIG. 1. An absorption site may be made of, for example, paper, and it may be used in the form of an absorbent pad.

In the immunochromatographic detection apparatus of the present invention, an end of a solid-phase support may be used as a specimen supply site, or a specimen supply site may be made of a material other than the solid-phase support. In the case of the latter, the specimen supply site is provided in contact with the solid-phase support, so that a solution can spread and move by the capillary flow. That is, the specimen supply site once absorbs the specimen or a mixture of the specimen and a labeled reagent and then supplies the absorbed specimen or mixture to the solid-phase support. Examples of materials other than the solid-phase support include, but are not particularly limited to, materials composed of naturally-occurring or synthetic polymers, such as nitrocellulose, cellulose acetate, nylon, polyethersulfone, polyvinyl alcohol, polyester, glass fiber, polyolefin, cellulose, and polystyrene, and a mixture of any thereof.

In the immunochromatographic detection apparatus of the present invention, a labeled reagent is a conjugate of an antibody that binds specifically to an antigen and an adequate labeled substance bound to each other. Examples of labeled substances include metal colloids such as gold colloids, nonmetal colloids such as selenium colloids, and insoluble substances such as colored resin particles (insoluble carriers). In general, a labeled reagent is allowed to impregnate into a material other than the solid-phase support, the resultant is dried, and it is then provided at a position connected to the solid-phase support. Alternatively, a label reagent may be directly applied to the solid-phase support and dried. When the specimen reaches the labeled reagent site containing a labeled reagent, the labeled reagent is dissolved in the specimen, and the resulting solution can then spread on the solid-phase support. Thus, the labeled reagent is retained in a labeled reagent site in a spreadable manner.

In the immunochromatographic detection apparatus of the present invention, a capture reagent is an antibody that binds specifically to an antigen, a capture reagent site can specifically bind to and capture a complex of an antigen and a labeled reagent, and a complex of a labeled reagent—an antigen—a capture reagent is thus formed. The presence of a complex can be detected visually on the basis of the color density of the line formed by the labeled substance in the capture reagent site 2, or it can be detected with the use of a measurement apparatus. In general, a capture reagent is prepared by directly applying the same to the solid-phase support and drying on the support. Alternatively, a capture reagent may be prepared by allowing the same to impregnate into a material other than the solid-phase support, drying the resultant, and the providing the same on the solid-phase support. A capture reagent can be immobilized on the solid-phase support via adsorption or other means without limitation. For example, a conventional technique, such as a method of chemical binding with the use of a functional group, such as an amino group or a carboxyl group, may be employed.

The antibody to be used as a capture reagent may be the same as the antibody to be used as a labeled reagent. When an antigen comprises only one site that binds to the substance of interest, however, a complex of a labeled reagent—an antigen—a capture reagent is not formed. In such a case, accordingly, it is necessary that the capture reagent be bound to a site of the antigen that is different from a site to which the labeled reagent binds.

A solid-phase support may be made of any substance, provided that it absorbs a sample specimen and allows the same to flow through capillary action. For example, a support is composed of a substance selected from the group consisting of naturally-occurring or synthetic polymers, such as nitrocellulose, cellulose acetate, nylon, polyethersulfone, polyvinyl alcohol, polyester, glass fiber, polyolefin, cellulose, and polystyrene, and a mixture of any thereof. A solid-phase support is preferably in the form of a strip.

Hereafter, a method for detecting PBP2' directly from a blood-culture-positive specimen via immunochromatography is described in detail.

Approximately 40% of the bacterial strains separated via blood culture are accounted for staphylococci. In the case of staphylococci, many cells resistant to antibiotics, such as methicillin resistant *staphylococcus aureus* (MRSA), have developed. In order to achieve rapid and adequate treatment of septicemia, it is necessary that the presence or absence of resistance be determined. Penicillin binding protein 2' (PBP2') is known as a protein associated with drug resistance of staphylococci.

The present invention provides a method for detecting PBP2' within a shorter period of time without culture comprising directly testing specimens that were found staphylococci-positive as a result of blood culture.

A blood sample is obtained from a patient suspected of septicemia, and culture is initiated with the use of a blood culture apparatus such as BacT/Alert. When bacterial growth was observed in the specimen alerted by the apparatus, 1 ml thereof is sampled, 1 ml of a mixture of 0.1M sodium hydroxide and 1.5% TRITON X-100 is added, and blood cells are destructed rapidly. The whole amount of the treated specimens is allowed to pass through a filter membrane with a pore size smaller than the bacterial cells. Thus, the target bacteria are captured on the filter membrane. The target protein (PBP2') is present on a bacterial cell membrane. In order to detect the target protein with high sensitivity, accordingly, it is necessary to destruct the cells. A mixture (1 ml) of 0.2 M sodium hydroxide and 1.0% TRITON X-100 is allowed to pass through the filter, and the filter is allowed to stand for 5 minutes, so as to destruct the cells and expose PBP2'. A neutralizing solution containing 0.6 M Tris-HCl is allowed to pass through the filter, and a PBP2'-containing filtrate is applied dropwise to an immunochromatographic test strip comprising a membrane on which antibodies that specifically capture PBP2' immobilized thereon and antibody-sensitized latex particles. Thus, PBP2' can be detected within a short period of time.

EXAMPLES

Hereafter, the present invention is described in greater detail with reference to the examples, although the technical scope of the present invention is not limited to these examples.

Example 1: Preparation of Immunochromatographic Test Strip for PBP2' Detection (1) Preparation and Drying of Antibody-Sensitized Latex Particles Anti-PBP2' monoclonal antibodies were treated with pepsin in accordance with a conventional technique to obtain F(ab')2. The obtained F(ab')2 was sensitized and bound to latex particles with a particle diameter of 0.4 µm, and the resultant was sprayed onto an unwoven polystyrene fabric. Subsequently, the resultant was dried under a reduced pressure in a pressure reducing device for 1 hour to obtain a dried latex antibody pad. At the time of use, the pad was cut at intervals of 4 mm and used as a labeled reagent site 2.

(2) Preparation of Immunochromatographic Test Strip for PBP2' Detection

The second anti-PBP2' monoclonal antibodies recognizing the site that is different from the site recognized by the anti-PBP2' monoclonal antibodies used for latex sensitization were treated with pepsin in accordance with a conventional technique to obtain F(ab')2. The obtained F(ab')2 was diluted in a citrate buffer (pH 6) containing 0.075% CHAPS, and the resultant was applied onto a nitrocellulose membrane (i.e., a solid-phase support 5), followed by thorough drying (i.e., a capture reagent site 3). As a control reagent, anti-mouse IgGs was applied to a nitrocellulose membrane in the same manner, and the resultant was thoroughly dried (i.e., a control site 4).

On a hydrophobic sheet 7, a solid-phase support 5 comprising the capture reagent site 3 and the control site 4 was provided, and the labeled reagent site 2, glass fiber as the specimen supply site 1, and a filter paper as the absorption site 6 were provided at arbitrary positions. Thus, an immunochromatographic test strip for PBP2' detection was prepared.

FIG. 1 shows the structure of the immunochromatographic test strip.

Example 2: Preparation of PBP2' Extraction Reagent

As a specimen suspension, an aqueous solution containing 0.1 M sodium hydroxide and 1.0% TRITON X-100 was prepared.

As R1 reagent (i.e., a microbial destruction reagent), an aqueous solution of 0.2 M sodium hydroxide and 1.5% Tx-100 was prepared.

As R2 reagent (i.e., a filtrate-adjusting solution), an aqueous solution of 0.6 M Tris-HCl (pH 6.0±0.5) was prepared.

The specimen suspension, the R1 reagent, and the R2 reagent are collectively referred to as "PBP2' extraction reagent."

Example 3: Examination of Filter Membrane Size

A cell suspension containing MRSA cultured in the blood agar medium at a density adjusted to $1.0 \times 10^8$ cells in physiological saline was designated as a specimen.
1) Specimen 1: A specimen suspension 1 was prepared and the total amount thereof was adjusted to 2 ml.
2) The total amount (2 ml) was filtered through a filter membrane made of cellulose acetate with a pore diameter of 0.45 μm and a diameter of 25 mm.
3) R1 reagent (1,000 μl) was filtered through the filter membrane of 2), the solution was retained in the filter membrane, and it was allowed to stand in that state for 5 minutes.
4) R2 reagent (400 μl) was filtered through the filter membrane of 3), and the filtrate was obtained.
5) The resultant was added dropwise to the specimen supply site on the PBP2' prepared in Example 1, and evaluation was performed 10 minutes later. The results of evaluation are shown in Table 1. The symbol "++" indicates a relatively strong positive and the symbol "+++" indicates a strong positive.

TABLE 1

| Filter | Material | Pore diameter (mm) | Diameter (mm) | Results of evaluation |
| --- | --- | --- | --- | --- |
| 1 | PVDF | 0.22 | 33 | +++ |
| 2 | PVDF | 0.45 | 33 | +++ |

TABLE 1-continued

| Filter | Material | Pore diameter (mm) | Diameter (mm) | Results of evaluation |
| --- | --- | --- | --- | --- |
| 3 | PVDF | 0.8 | 33 | ++ |
| 4 | Acrylic copolymer | 1.2 | 25 | ++ |

PVDF: Polyvinylidene fluoride

The results shown in Table 1 demonstrate that PBP2' of MRSA can be detected by the method of the present invention with the use of a filter membrane with a pore diameter of 0.22 to 1.2 μm. Particularly satisfactory results are attained with the use of a filter membrane with a pore diameter of 0.22 to 0.45 μm Example 4: Examination of Filter Membrane Material A cell suspension containing MRSA cultured in the blood agar medium at a density adjusted to $1.0 \times 10^8$ cells in physiological saline was designated as a specimen.
1) Specimen 1: A specimen suspension 1 was prepared and the total amount thereof was adjusted to 2 ml.
2) The total amount (2 ml) was filtered through a filter membrane made of cellulose acetate with a pore diameter of 0.45 μm and a diameter of 25 mm.
3) R1 reagent (1,000 μl) was filtered through the filter membrane of 2), the solution was retained in the filter membrane, and it was allowed to stand in that state for 5 minutes.
4) R2 reagent (400 μl) was filtered through the filter membrane of 3), and the filtrate was obtained.
5) The resultant was added dropwise to the specimen supply site on the PBP2' prepared in Example 1, and evaluation was performed 10 minutes later. The results of evaluation are shown in Table 2. The symbol "++" indicates a relatively strong positive and the symbol "+++" indicates a strong positive.

TABLE 2

| Filter | Material | Pore diameter (mm) | Diameter (mm) | Results of measurement |
| --- | --- | --- | --- | --- |
| 1 | PVDF | 0.45 | 33 | +++ |
| 2 | MCE | 0.45 | 33 | ++ |
| 3 | PES | 0.45 | 33 | ++ |
| 4 | Hydrophilic polyethersulfone | 0.45 | 32 | +++ |
| 5 | GHP | 0.45 | 25 | +++ |
| 6 | PVDF | 0.45 | 25 | +++ |
| 7 | NYL + GxF | 0.45 | 25 | +++ |
| 8 | PES + GxF | 0.45 | 25 | +++ |
| 9 | CA + GF | 0.45 | 33 | +++ |
| 10 | NYL + GF | 0.45 | 33 | ++ |
| 11 | Cellulose acetate | 0.45 | 25 | +++ |
| 12 | PES | 0.45 | 25 | +++ |
| 13 | Hydrophilic PTFE | 0.45 | 25 | +++ |

PVDF: Polyvinylidene fluoride
MCE: Mixed cellulose ester
PES: Polyethersulfone
GHP: Hydrophilic polypropylene
NYL: Nylon
CA: Cellulose acetate
GxF: Multi-layer glass fiber prefilter
GF: Borosilicate glass fiber prefilter
PTFE: Polytetrafluoroethylene The results shown in Table 2 demonstrate that PBP2' of MRSA can be detected by the method of the present invention with the use of any of the filter membranes 1 to 13.

Example 5: Examination of Surfactant

A cell suspension containing MRSA cultured in the blood agar medium at a density adjusted to $1.0 \times 10^8$ cells in physiological saline was designated as a specimen.
1) Specimen 1: A specimen suspension 1 was prepared and the total amount thereof was adjusted to 2 ml.
2) The total amount (2 ml) was filtered through a filter membrane made of cellulose acetate with a pore diameter of 0.45 μm and a diameter of 25 mm.
3) R1 reagent (1,000 μl) was filtered through the filter membrane of 2), the solution was retained in the filter membrane, and it was allowed to stand in that state for 5 minutes.
4) R2 reagent (400 μl) was filtered through the filter membrane of 3), and the filtrate was obtained.
5) The resultant was added dropwise to the specimen supply site on the PBP2' test piece prepared in Example 1, and evaluation was performed 10 minutes later. The results of evaluation are shown in Table 3. The symbol "++" indicates a relatively strong positivity and the symbol "+++" indicates a strong positivity.

TABLE 3

| Surfactant | Results of measurement |
| --- | --- |
| Tx-100 | +++ |
| Tx-405 | +++ |
| Tween 20 | +++ |
| Tween 80 | +++ |
| Brij35 | +++ |
| Emulgen 106 | +++ |
| Emulgen A500 | +++ |
| SDS | +++ |
| CHPAS | +++ |
| Dodecyl trimethyl ammonium chloride | +++ |

Emulgen 106: Polyoxyethylene (5) lauryl ether
Emulgen A500: Polyoxyethylene distyrene-modified phenyl ether The results shown in Table 3 demonstrate that PBP2' of MRSA can be detected by the method of the present invention with the use of any surfactant.

Example 6: Experiment for Comparison with Conventional Technique

The filter membrane technique according to the present invention was compared with a conventional technique of centrifugation in terms of reproducibility.

The specimen was prepared by diluting the MRSA cells in a blood medium (defibrinated horse blood:liquid medium (1:4)).

1. Centrifugation
1) Specimen 1: A specimen suspension 3 was prepared and the total amount thereof was adjusted to 2 ml.
2) Centrifugation was carried out at 7,000 g and room temperature for 5 minutes. 3) The supernatant was discarded and 200 μl of R1 reagent was added.
4) R2 reagent (100 μl) was mixed therewith.
5) The resultant was added dropwise to the specimen supply site on the PBP2' test piece prepared in Example 1, and evaluation was performed 10 minutes later.

2. Filter Membrane Technique
1) Specimen 1: A specimen suspension 1 was prepared and the total amount thereof was adjusted to 2 ml.
2) The total amount (2 ml) was filtered through a filter membrane made of cellulose acetate with a pore diameter of 0.45 μm and a diameter of 25 mm.
3) R1 reagent (1,000 μl) was filtered through the filter membrane of 2), the solution was retained in the filter membrane, and it was allowed to stand in that state for 5 minutes.
4) R2 reagent (400 μl) was filtered through the filter membrane of 3), and the filtrate was collected.
5) The resultant was added dropwise to the specimen supply site on the PBP2' test piece prepared in Example 1, and evaluation was performed 10 minutes later.

The centrifugation technique and the filter membrane technique were performed 3 times by Testers A, B, and C, and reproducibility of the results of evaluation was compared. The results of evaluation are shown in Table 4. The symbol "−" indicates a negative, the symbol "+" indicates a positive, the symbol "++" indicates a relatively strong positive, and the symbol "+++" indicates a strong positive.

TABLE 4

| | Centrifugation technique | | | Filter membrane technique | | |
| --- | --- | --- | --- | --- | --- | --- |
| | n = 1 | n = 2 | n = 3 | n = 1 | n = 2 | n = 3 |
| A | ++ | + | +++ | +++ | +++ | ++ |
| B | + | ++ | ++ | +++ | +++ | ++ |
| C | + | ± | − | +++ | ++ | ++ |

The results shown in Table 4 demonstrate that reproducibility achieved by the filter membrane technique of the present invention is superior to that achieved by a conventional centrifugation technique.

INDUSTRIAL APPLICABILITY

According to the method of the present invention, infectious diseases caused by pathogenic microorganisms and the presence of pathogenic microorganisms can be detected.

DESCRIPTION OF NUMERICAL REFERENCES

1: Specimen supply site
2: Labeled reagent site
3: Capture reagent (capture antibody) site
4: Control site
5: Solid-phase support (nitrocellulose membrane)
6: Absorption site (absorbent pad)
7: Top laminate or housing All publications, patents, and patent applications cited herein are incorporated herein by reference in their entirety.

The invention claimed is:

1. A method for collecting antigens of microorganisms comprising: allowing specimens containing microorganisms to pass through a filter membrane with a pore diameter that does not allow the microorganisms to pass therethrough; capturing the microorganisms in the specimens on the filter membrane; allowing a microbial destruction reagent capable of microbial membrane destruction to pass through the filter membrane on which the microorganisms are captured to destruct the captured microorganisms on the filter membrane; and collecting the antigens in the filtrate, wherein the microbial destruction reagent is a surfactant, an alkaline solution, or a mixture of a surfactant and an alkaline solution.

2. The method for collecting antigens of microorganisms according to claim 1, wherein the microorganisms are bacteria.

3. The method for collecting antigens of microorganisms according to claim 1, wherein the microbial destruction reagent is a mixture of a surfactant and an alkaline solution.

4. The method for collecting antigens of microorganisms according to claim 3, wherein the alkaline solution has a pH of 11 or higher.

5. The method for collecting antigens of microorganisms according to claim 3, wherein the alkaline solution is a sodium hydroxide solution.

6. A method for detecting microorganisms comprising assaying the microbial antigens collected by the method according to claim 1 by an immunoassay technique.

7. The method for detecting microorganisms according to claim 6, wherein the immunoassay technique is immunochromatography.

8. A method for detecting microorganisms comprising assaying the microbial antigens collected by the method according to claim 2 by an immunoassay technique.

9. A method for detecting microorganisms comprising assaying the microbial antigens collected by the method according to claim 3 by an immunoassay technique.

10. A method for detecting microorganisms comprising assaying the microbial antigens collected by the method according to claim 4 by an immunoassay technique.

11. A method for detecting microorganisms comprising assaying the microbial antigens collected by the method according to claim 5 by an immunoassay technique.

12. The method for detecting microorganisms according to claim 8, wherein the immunoassay technique is immunochromatography.

13. The method for detecting microorganisms according to claim 9, wherein the immunoassay technique is immunochromatography.

14. The method for detecting microorganisms according to claim 10, wherein the immunoassay technique is immunochromatography.

15. The method for detecting microorganisms according to claim 11, wherein the immunoassay technique is immunochromatography.

* * * * *

UNITED STATES PATENT AND TRADEMARK OFFICE
CERTIFICATE OF CORRECTION

| | | |
|---|---|---|
| PATENT NO. | : 10,436,783 B2 | Page 1 of 1 |
| APPLICATION NO. | : 15/569143 | |
| DATED | : October 8, 2019 | |
| INVENTOR(S) | : Saito et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 29 days.

Signed and Sealed this
Twenty-eighth Day of July, 2020

Andrei Iancu
*Director of the United States Patent and Trademark Office*